(12) United States Patent
Rifai

(10) Patent No.: US 8,507,461 B2
(45) Date of Patent: Aug. 13, 2013

(54) NON-ABSORBABLE NON-DIGESTIBLE POLYMER COMPOUNDS

(76) Inventor: Abdalla Rifai, Glocester, RI (US)

( * ) Notice: Subject to any disclaimer, the term of this patent is extended or adjusted under 35 U.S.C. 154(b) by 875 days.

(21) Appl. No.: 11/991,516

(22) PCT Filed: Sep. 6, 2006

(86) PCT No.: PCT/US2006/034708
§ 371 (c)(1),
(2), (4) Date: Mar. 31, 2009

(87) PCT Pub. No.: WO2007/070135
PCT Pub. Date: Jun. 21, 2007

(65) Prior Publication Data
US 2009/0247484 A1 Oct. 1, 2009

Related U.S. Application Data

(60) Provisional application No. 60/714,375, filed on Sep. 6, 2005.

(51) Int. Cl.
| | | |
|---|---|---|
| A61K 31/734 | (2006.01) | |
| A23L 1/0532 | (2006.01) | |
| A61P 3/10 | (2006.01) | |
| C08B 37/00 | (2006.01) | |
| C08B 37/02 | (2006.01) | |
| C08B 37/04 | (2006.01) | |
| C08B 37/06 | (2006.01) | |
| C08B 37/08 | (2006.01) | |
| C08B 37/10 | (2006.01) | |
| C08B 37/12 | (2006.01) | |
| C08B 37/14 | (2006.01) | |
| C08B 37/16 | (2006.01) | |

(52) U.S. Cl.
USPC .......... 514/54; 514/55; 514/56; 514/57; 514/58; 514/59; 514/60; 536/3; 536/30; 536/45; 536/102; 536/112; 536/123.1

(58) Field of Classification Search
None
See application file for complete search history.

(56) References Cited

U.S. PATENT DOCUMENTS

| | | |
|---|---|---|
| 5,324,526 A * | 6/1994 | Iwata et al. .......... 426/2 |
| 5,496,545 A | 3/1996 | Holmes-Farley et al. |
| 5,607,669 A | 3/1997 | Mandeville, III et al. |
| 5,618,530 A | 4/1997 | Mandeville, III et al. |
| 5,667,775 A | 9/1997 | Holmes-Farley et al. |
| 5,693,675 A | 12/1997 | Mandeville, III et al. |
| 5,919,832 A | 7/1999 | Mandeville, III et al. |
| 5,925,379 A | 7/1999 | Mandeville, III et al. |
| 6,187,762 B1 | 2/2001 | Mandeville, III et al. |
| 6,203,785 B1 | 3/2001 | Holmes-Farley et al. |
| 6,235,305 B1 | 5/2001 | Mullins |
| 6,248,318 B1 | 6/2001 | Huval et al. |
| 6,264,937 B1 | 7/2001 | Mandeville, III et al. |
| 6,267,952 B1 | 7/2001 | Mandeville, III et al. |
| 6,294,163 B1 | 9/2001 | Dhal et al. |
| 6,299,868 B1 | 10/2001 | Jozefiak et al. |
| 6,352,692 B1 | 3/2002 | Mandeville, III et al. |
| 6,423,754 B1 | 7/2002 | Holmes-Farley et al. |
| 6,509,013 B1 | 1/2003 | Holmes-Farley et al. |
| 6,534,087 B2 | 3/2003 | Busson et al. |
| 6,558,657 B1 | 5/2003 | Mandeville, III et al. |
| 6,572,850 B1 | 6/2003 | Mandeville, III et al. |
| 6,756,364 B2 | 6/2004 | Barbier et al. |
| 2004/0087514 A1 | 5/2004 | Hughes et al. |

FOREIGN PATENT DOCUMENTS

| | | |
|---|---|---|
| EP | 1123975 | 8/2001 |
| EP | 1362869 | 11/2003 |
| EP | 1389621 | 2/2004 |
| WO | WO 02/40055 | 5/2002 |

OTHER PUBLICATIONS

Donati, I. et al "Galactose-substituted alginate . . . " Biomacromolecules (2003) vol. 4, pp. 624-631.*
Yamatoya, K. et al "Effects of hydrolyzed guar gum on cholesterol and glucose . . . " Food Hydrocolloids (1997) vol. 11, No. 2, pp. 239-242.*
Choi et al. "A Colorimetric Microplate Assay Method for High Throughput Analysis of Lipase Activity." 2003, J. Biochem. Mol. Biol., vol. 36(4), pp. 417-420.
Plotz et al. "Stable, Soluble Model Immune Complexes Made With a Versatile Multivalent Affinity-Labeling Antigen." 1982, Biochemistry, vol. 21, pp. 301-308.

* cited by examiner

*Primary Examiner* — Leigh Maier
(74) *Attorney, Agent, or Firm* — Henry J. Cittone; Cittone & Chinta LLP

(57) ABSTRACT

The present invention relates to compounds which are capable of exerting an inhibitory effect on the Na+ glucose cotransporter SGLT in order to hinder glucose and galactose absorption, as well as on lipase thus reducing dietary triglyceride metabolism, for use in the treatment of conditions which benefit therefrom (diabetes, Metabolic Syndrome, obesity, prevention of weight gain or aiding weight loss). These compounds comprise a non-absorbable, non-digestible polymer having a glucopyranosyl or galactopyranosyl or equivalent moiety stably and covalently linked thereto, said glucopyranosyl or galactopyranosyl moiety being able to occupy the glucose-binding pocket of a SGLT transporter.

3 Claims, 4 Drawing Sheets

NON-ABSORBABLE NON-DIGESTIBLE POLYMER COMPOUNDS

CROSS REFERENCE TO RELATED APPLICATIONS

The present application is a National Phase Application of International Application No. PCT/US2006/034708, filed Sep. 6, 2006, which claims priority to U.S. Patent Application No. 60/714,375 filed Sep. 6, 2005, which applications are incorporated herein fully by this reference.

The present invention relates to compounds which are capable of exerting an inhibitory effect on the Na$^+$ glucose cotransporter SGLT and on lipase and uses thereof, in particular the use thereof to treat diabetes, Metabolic Syndrome, obesity and related disorders.

Diabetes mellitus is a worldwide epidemic that affects more than 170 million individuals. Approximately 90% of diabetic individuals have type 2 (non-insulin-dependent) diabetes. Elevated blood glucose levels, hyperglycemia, is characteristic of diabetes and considered to be the major risk factor for onset of diabetic complications. Diabetes mellitus is diagnosed on the basis of WHO recommendations from 1999, incorporating both fasting and 2-h after glucose load (75 g) oral glucose tolerance test.

The Metabolic Syndrome is a constellation of metabolic abnormalities (impaired glucose tolerance, insulin resistance, dyslipidaemia, hypertension and obesity). The Metabolic Syndrome is associated with an increased risk of both diabetes and cardiovascular diseases. It is well recognized that the worldwide obesity epidemic is the most important driving force in the recognition of the metabolic syndrome disorder as a prelude to diabetes.

Obesity is a growing problem, especially in the western world. Over a third of American adults are clinically obese, with 3 million adults suffering from life-threatening obesity. In the UK, 20% of adults are clinically obese and this number is on the rise and is predicted to reach 25% by 2010. A major cause is excessive consumption of carbohydrates and lipids. Modern food stuffs are typically high in fat and carbohydrates and in many countries food is available in abundance. This leads many people to consume excessive amounts of carbohydrates and fat. Many people find it difficult to restrict their diet and/or to exercise more. There is a growing demand for compositions which aid weight loss and/or inhibit weight gain.

The fat contained in foods is predominantly present in the form of triglycerides. An important catalyst in the digestion of dietary triglycerides are lipases. "Lipases" as used herein, are enzymes that hydrolyze ester bonds in triglycerides. Examples of lipases include gastric, pancreatic and lingual lipase. Pancreatic lipase, being the predominant intestinal enzyme, cleaves the primary ester bond of triglycerides to release free fatty acids and monoglyceride, which can be absorbed through the intestinal wall and hence enter the blood stream. Undigested triglycerides can not be absorbed efficiently and inhibition of lipase, in particular pancreatic lipase, may therefore lead to the excretion of a significant proportion of dietary triglycerides.

Carbohydrates are typically present in food stuffs in the form of free glucose, or in the form of complex carbohydrates. Carbohydrates in the diet are converted to free monosaccharides before absorption as a result of the concerted action of salivary and pancreatic amylases and the brush border disaccharidases. The carbohydrates in the diet are then presented to the intestinal epithelium as glucose, galactose and fructose monosaccharides.

Monosaccharides are essentially the only form of dietary carbohydrates that are efficiently absorbed in the intestine. Intestinal glucose and galactose uptake is mediated by sodium-dependent glucose co-transporters, SGLT, located on the surface of the epithelial cells lining the small intestine. There are several types of SGLT, and SGLT1 and SGLT2 are of particular interest according to the present invention, with SGLT1 being of most particular interest. Glucose and galactose are transported from the intestinal lumen into the epithelial cells of the intestine, and passively pass out of these cells across the basolateral membrane through the uniporter (GLUT2) into the blood stream.

Approaches to try and reduce excessive calorie uptake include modulation of the neuroendocrine pathways to reduce appetite and inhibition of the intestinal absorption of fats or carbohydrates. Drugs which modulate appetite are often associated with undesirable, often dangerous side effects.

"Lipase inhibitors" as used herein refers to compounds that are capable of inhibiting the action of lipases. Lipstatin and its derivative tetrahydrolipstatin, also known as Orlistat, as disclosed in U.S. Pat. No. 4,598,089, are potent inhibitors of gastric and pancreatic lipases as well as cholesterol ester hydrolase. However this inhibitory action is associated with various unpleasant side effects including fecal incontinence.

The present inventor has surprisingly found a way to inhibit the metabolism of fats as well as to inhibit glucose and galactose uptake without modulating the neuroendocrine pathways. He has developed a class of compounds which are capable of inhibiting the glucose co-transporters, SGLT, and/or of inhibiting the metabolism of triglycerides by lipases. Compounds of the invention are capable of inhibiting one or more forms of SGLT, preferably SGLT1. In a preferred embodiment gastric and/or pancreatic lipase (as well as the glucose transporter) is inhibited, most preferably pancreatic lipase. This dual activity was highly unexpected, because these two processes are unrelated and involve completely different components of the cellular machinery.

Although compounds which are capable of inhibiting the glucose co-transporters, SGLT, and of inhibiting the metabolism of triglycerides by lipases are preferred, compounds which are capable of inhibiting the glucose co-transporters, SGLT, and which have only little or no measurable effect on the metabolism of triglycerides by lipases are another aspect of the present invention. Yet another aspect of the invention are compounds which are capable of inhibiting the metabolism of triglycerides by lipases and which have only little or no measurable effect on the activity of the glucose transporters, SGLT. Thus, any discussion of compounds, methods, uses, kits and the like provided below is to be understood also to refer to any of these compounds.

Thus, according to one aspect, the present invention provides a non-absorbable non-digestible polymer having glucose, galactose or a derivative thereof stably and covalently linked thereto. "Derivative" as used herein refers to any compound containing the essential elements of the parent substance, glucose and galactose being the parent substances.

Alternatively viewed, the present invention provides a non-absorbable non-digestible polymer having a glucopyranosyl or galactopyranosyl or equivalent moiety stably and covalently linked thereto.

Preferably the glucopyranosyl or galactopyranosyl or equivalent moiety can occupy the glucose-binding pocket of the SGLT transporter, in particular the SGLT1 transporter.

Thus, the present invention provides compounds which comprise, consist essentially of or consist of a non-absorbable non-digestible polymer having a glucopyranosyl, galactopyranosyl or equivalent moiety stably and covalently linked thereto. Preferably, the compounds of the invention consist essentially of a non-absorbable non-digestible polymer having a glucopyranosyl, galactopyranosyl or equivalent moiety stably and covalently linked thereto.

The compounds of the invention are not naturally occurring. They may consist of naturally occurring polymers which have been modified, in particular modified by the covalent addition of a glucopyranosyl, galactopyranosyl or equivalent moiety thereto. Alternatively the polymer itself may be non-naturally occurring.

In a preferred embodiment, the invention provides a non-absorbable non-digestible polymer having a glucopyranosyl or galactopyranosyl or equivalent moiety stably and covalently linked thereto but excluding Ficoll-AECM-Gal and Ficoll-AECM-Mannose.

It has surprisingly been found that certain of these compounds have a dual effect, being capable of inhibiting the SGLT glucose co-transporter as well as being capable of inhibiting lipase activity. Preferred compounds have the ability to inhibit SGLT-1 and SGLT-2, but some compounds may only inhibit one of the SGLT types. For example, SGLT-2 typically only recognises galactose very poorly, so compounds with a galactopyranosyl moiety may only be able to inhibit SGLT1 but not SGLT2.

Without wishing to be bound by theory, it is believed that the glucopyranosyl, galactopyranosyl or equivalent moiety fits into the glucose-binding pocket of the SGLT transporter. This pocket normally accepts glucose or galactose and the transporter then mediates transfer of these compounds across the cell membrane. It is thought that the pyranosyl moiety of the compounds of the present invention can interact with the SGLT transporter, but due to the presence of the polymer to which the pyranosyl moiety is linked, transport across the cell membrane is prohibited. In other words, linkage of the glucopyranosyl, galactopyranosyl or equivalent moiety to the polymer renders it essentially non-absorbable.

During this interaction between the polymer attached glucopyranosyl/galactopyranosyl moiety and the SGLT, the transporter is not available to transport free glucose molecules, i.e. it is blocked. Consequently, any dietary glucose or galactose which is present in the intestine at the same time as the compound of the present invention is thought to have to compete with the compound of the present invention for access to the SGLT transporter. At least a proportion of the glucose molecules which compete unsuccessfully for access to the SGLT transporter are eventually excreted from the bowel.

The interaction between the compounds of the present invention and the SGLT transporter is preferably reversible, i.e. the polymer attached pyranosyl moiety will eventually be released from the SGLT pocket.

The compounds of the present invention preferably also have an inhibitory effect on lipase, preferably on pancreatic lipase. Without wishing to be bound by theory, it is believed that the glucopyranosyl, galactopyranosyl or equivalent moiety may interact with the active site of lipase, thus preventing access of the normal substrate to the lipase active site. This may lead to competition between triglycerols, i.e. the natural substrate for lipase, and the compounds of the present invention for access to the lipase, leading to the excretion of dietary triglycerides.

In a preferred embodiment, the compounds of the present invention have an overall positive charge, and this charge may allow these compounds to interact with the lipase, which may prevent triglycerides from interacting with the lipase due to steric hindrance. It is also possible that the compounds of the present invention may bind triglycerides and thereby prevent the triglycerides from being able to interact with lipase.

These surprising findings are illustrated in the Examples disclosed herein. The lipase inhibitory properties of selected examples of compounds of the present invention are shown in Examples 3-7 and 11 and the inhibitory effect on glucose transport is shown in Examples 8 and 11.

The "polymer" is essentially inert and serves to provide a backbone or scaffold for the glucopyranosyl, galactopyranosyl or equivalent moiety. Suitable polymers are discussed below but no minimum number of monomer sub-units is implied by this term.

Preferably, the polymer part is cationic. The term "cationic polymer" as used herein refers to a polymer which bears a positive charge at physiological pH. Such a polymer may have basic groups along the polymer backbone. A basic group is a group that is protonated at physiological pH to form a cationic group. Cationic polymers include polymers composed of primary, secondary or tertiary amine groups and/or quaternary ammonium groups. Other polymers and methods of preparation, which can be used in the claimed invention have been disclosed and reported in the patent literature in, for example, U.S. Pat. Nos. 5,496,545, 5,607,669, 5,618,530, 5,667,775, 5,693,675, 5,919,832, 5,925,379, 6,187,762, 6,203,785, 6,248,318, 6,264,937, 6,267,952, 6,294,163, 6,299,868, 6,352,692, 6,423,754, 6,509,013, 6,558,657, 6,572,850 all of which incorporated herein by reference.

Polymers which are initially neutral or anionic may also be used to prepare the compounds of the present invention, preferably they are modified to become cationic.

An overall positive charge may have many desired effects. For example, it may enhance the polymer's ability to bind bile acids and free fatty acids. Polyanionic polymers such as carboxymethylcellulose, alginate, pectin and the like are thus preferably rendered cationic through conjugation to suitable cationic moieties such as aminoethyl.

The polymer may be naturally occurring or synthetic. Examples of suitable cationic synthetic polymers include, polyallylamine, polylysine polyethyleneimine, polyvinylamine, and other polymers disclosed and reported in the patent literature referenced above. The polymer preferably having a molecular weight greater than 3 kDa, more preferably greater than 8 kDa.

The polymer may be linear or branched and may be of the block co-polymer, alternating repeat, interrupted repeat or complex repeat type.

Examples of suitable natural, modified and synthetic polymers are known in the art. Preferred polymers include Alginate, soluble and insoluble β-glucan, microcrystalline cellulose, modified cellulose such as methylcellulose, carboxymethylcellulose, methyl hydroxypropyl cellulose Chitosan, cyclodextrins, dextran, gellan gum, xanthan gum, acacia gum, Carrageenan, Agar, Pectin, fructans including levan and inulin, galactomannan, guar gum, locust bean gum, gum karaya, gum tragacanth, resistant starch, Konjac mannan, pullulan, and sucrose polymers such as Ficoll™. Preferred polymers include those disclosed herein in the Examples.

Synthetic, preferably polycationic polymers are preferred, especially nitrogen containing polymers. Particularly preferred polymers are polyallylamine, polylysine and polyethyleneimine and derivatives thereof. Polyallylamine is most preferred together with derivatives of it as described in U.S. Pat. No. 4,680,360.

By "synthetic" polymer is meant a polymer which is not naturally occurring, i.e. a polymer which is not naturally produced by plants, animals, bacteria or fungi.

A further group of suitable polymers include the following:

Representative synthetic polymers include alkyl cellulose, cellulose esters, cellulose ethers, hydroxyalkyl celluloses, nitrocelluloses, poly[lactide-co-glycolide], polyalkylene glycols, polyalkylene oxides, polyalkylene terephthalates, polyalkylenes polyamides, polyanhydrides, polycarbonates, polyglycolides, polymers of acrylic and methacrylic esters, polysiloxanes, polyurethanes, polyvinyl alcohols, polyvinyl esters, polyvinyl ethers, polyvinyl halides, polyvinylpyrrolidone, polyorthoester blends and copolymers thereof.

Specific examples of these polymers include cellulose acetate, cellulose propionate, cellulose acetate butyrate, cellulose acetate phthalate, carboxymethyl cellulose, cellulose triacetate, cellulose sulphate, poly(methyl methacrylate), poly(ethyl methacylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene and polyvinylpyrrolidone, polyurethane, polylactides, poly(butyric acid), poly(valeric acid), poly[lactide-co-glycolide], polyanhydrides, polyorthoesters, poly(fumaric acid), and poly(maleic acid).

The polymer will preferably have linked thereto more than one glucopyranosyl, galactopyranosyl or equivalent moiety. For example, glucopyranosyl, galactopyranosyl or equivalent moieties may be conjugated to 10-20% of the units composing the polymer backbone, but polymers in which 40 to 60% or 60 to 80% or more of the units composing the polymer backbone are conjugated are also contemplated. Thus, typically 5-90%, e.g. 10-80%, of the polymer subunits may carry a pyranosyl moiety as defined above, preferably between 10 and 50%, e.g. 20-40%.

The compounds of the present invention will preferably comprise at least 5 glucopyranosyl, galactopyranosyl or equivalent moieties conjugated to the polymer backbone, more preferably at least 10, 15 or 20, most preferably at least 30. In a preferred embodiment the compounds comprise a maximum of 200 glucopyranosyl, galactopyranosyl or equivalent moieties conjugated to the units composing the polymer backbone, more preferably less than 150. Thus the compound may preferably comprise 5-100, more preferably 10-50, e.g. 15-30 glucopyranosyl, galactopyranosyl or equivalent moieties conjugated to the polymer backbone.

The polymer may preferably have further features which confer fat-binding properties to the polymer. Such features include the presence of a hydrophobic alkyl moiety such as octyl, lauryl, stearyl and the like which allow the polymer to bind to chylomicron micelles. Fat binding may have dual effect. It may prevent the (pancreatic) lipase from gaining access to its substrate. It may also reduce or prevent the occurrence of steatorrhea, thus alleviating any unpleasant side effects which may otherwise occur.

By "non-absorbable" is meant that the polymer is not readily absorbed in the stomach or intestine of the subject, and hence it does not enter the blood stream in any significant amounts. It is to be understood that the term "non-absorbable" is not absolute, and small (i.e. calorifically insignificant) quantities of the polymer may therefore be absorbed.

The term "non-digestible" as used herein is to be understood to signify that the compound is essentially resistant to cleavage by the digestive system. Thus, the compound is resistant to enzymatic lysis and it is stable in the chemical environments of the stomach and intestine, i.e. it is resistant to chemical lysis in those environments. Again, there may be small amounts of degradation but any breakdown products will be calorifically insignificant in terms of acting as a nutrient source for the subject.

By "glucopyranosyl, galactopyranosyl or equivalent moiety" is meant any chemical moiety which is structurally and functionally equivalent to glucopyranose or galactopyranose. Included are acid, base, or alcohol derivatives of α-D-glucopyranose, β-D-glucopyranose, α-L-glucopyranose, β-L-glucopyranose, α-D-galactopyranose, β-D-galactopyranose, α-L-galactopyranose, β-L-galactopyranose, and the pyranose forms (including alpha or beta forms in D or L configuration) of e.g. allose, altrose, mannose, gulose, idose and talose. Any other moieties which are structurally and functionally equivalent to any of the hexoses named above are also intended to be covered by the term "glucopyranosyl, galactopyranosyl or equivalent moiety".

To be considered "equivalent", a moiety should (under identical environmental conditional such as pH, temperature and the like) occupy a substantially similar three-dimensional space as the examples listed above. Equivalent moieties will typically be similar in size, overall spatial configuration and charge.

A single 6-membered ring structure is required, which will typically be formed of 5 carbon atoms and one oxygen atom. Preferably, the linked moiety is glucopyranose or galactopyranose.

Modifications which do not have a significant effect on the structure and function of the moiety and which therefore fall within the present definition of the term "glucopyranosyl, galactopyranosyl or equivalent moiety" may typically include the replacement of one or more atoms or groups with equivalent atoms or groups of similar size and charge, or the addition of a small group, such as methyl, at a suitable position. A suitable example is methyl-D-glucoside.

Thus, mimetics of glucopyranose and galactopyranose are encompassed within the definition, a mimetic being a molecule which is similarly able to occupy the glucose-binding pocket of the SGLT transporter, in particular of SGLT1. This ability may be readily determined by 3-D computational analysis or by performing an in vitro assay relying on competitive inhibition of the transporter.

Preferably, the glucopyranosyl, galactopyranosyl or equivalent moiety is pharmacologically safe, both in its free form and when linked to the polymer. By "pharmacologically safe" is meant that the moiety (or any metabolites thereof produced when said moiety is administered to a subject) does not cause any clinically significant toxic effects when present at clinically or cosmetically useful levels in a subject. Although the glucopyranosyl, galactopyranosyl or equivalent moiety is stably and covalently linked to the polymer, some cleavage separating the moiety from the polymer may occur, so it is desired the moiety be pharmacologically safe even when present in its free form.

The preferred groups attached to the polymer are glucopyranosyl or galactopyranosyl groups, preferably in the D-form, glucopyranose being especially preferred.

Further, the glucopyranosyl, galactopyranosyl or equivalent moiety defined above may be part of a disaccharide or trisaccharide or oligosaccharide, e.g. of up to 10 monosaccharide sub units, which is linked to the polymer. Typically this pyranosyl moiety will be at the end which is remote from the polymer to facilitate interaction with SGLT etc. The disaccharide, trisaccharide or oligosaccharide should be resistant to the glucosidase in the brush border, i.e. it is important that the glucopyranosyl, galactopyranosyl or equivalent moiety is not cleaved but remains stably and covalently linked to the polymer. Disaccharides are preferred and these include lactose and derivatives thereof including lactobionic acid, lactulose and lactitol. For example, lactobionic acid may be conjugated to the polymer via the gluconic acid in an open configuration such that the galactose moiety in ring form is available (and not hydrolysable) to act as a SGLT blocker.

The glucopyranosyl, galactopyranosyl or equivalent moiety must be stably linked to the polymer. Within the meaning of the present invention, "stably linked" is to be understood to mean attached to the polymer via a suitable bond, either directly or via a suitable spacer as defined below. Suitable bonds include amide bonds, ether bonds, disulfide bonds and the like. Suitable agents which may be used to facilitate linkage of the glucopyranosyl moiety to the polymer are known in the art and include, for example, the carbodiimide compounds EDAC or EDC.

The resulting bond must be stable, i.e. it must be essentially resistant to cleavage, whether chemical or enzymatic, in the stomach and intestine of an animal subject. Indeed, any and all of the bonds between the glucopyranosyl, galactopyranosyl or equivalent moiety and the polymer must be stable.

In a preferred embodiment, the pyranosyl moiety is linked to the polymer through a "spacer" such as ethlenediamine, diaminopropylamine, diaminohexane and triethyleneglycoldiamine, alkyl diamines, phenyl triamines. The skilled person will be aware of suitable spacer molecules, but briefly, a suitable spacer molecule will have at least two, preferably two, functional groups for covalent cross-linking of two different molecules.

Preferably, the spacer is positively charged. Preferably the spacer does not include any cyclic groups. Preferably, the spacer does not comprise any aromatic moieties.

In general the spacer will have a length, from polymer backbone to pyranosyl moiety, of 2-20 linked non-hydrogen atoms, which may comprise carbon, nitrogen and/or oxygen, for example, but larger spacers are also envisaged, such as a bifunctional ethylene glycol linear polymer.

It must be understood that although the polymer may contain glucopyranosyl or galactopyranosyl subunits or derivatives thereof, the functional pyranosyl or equivalent moiety which must be linked to the polymer is distinct from such subunits. The bond between the gluco- or a galacto-pyranosyl moiety and the polymer is typically different from the bonds between the subunits of the polymer.

It is discussed above how compounds of the invention may be particularly advantageous because they can inhibit lipase activity and the SGLT transporter. In fact, certain compounds of the invention may only have one of these activities and yet nevertheless be useful in the various applications discussed herein. In particular, those compounds such as Glu-PEI (polyethyleneimine) which only inhibit the SGLT transporter. Inhibition of SGLT being a preferred activity and treatment of Type I diabetes being a preferred use of those compounds which only inhibit the SGLT transporter.

Glu-PEI is a preferred compound for use in treating Type 1 diabetes and Glu-PA (polyallylamine) is a preferred compound for use in treating Type 2 diabetes and/or obesity. Thus, PEI is a preferred polymer for use in treating Type 1 diabetes and PA is a preferred polymer for use in treating Type 2 diabetes and/or obesity.

In a further aspect, the present invention provides a pharmaceutical composition comprising the compounds of the invention as defined above, together with a pharmaceutically acceptable carrier, diluent or excipient.

Alternatively viewed the invention provides a composition comprising the compounds of the invention as defined above, together with a physiologically acceptable carrier, diluent or excipient.

The composition may comprise a single type of compound of the present invention, or a mixture of different types of compounds. Thus, it may comprise two or more different types of compounds which differ from one another in the type of polymer used, the type of bond between the pyranosyl moiety and the polymer, the type of pyranosyl moiety, the presence or absence of a spacer or the type of spacer, if present, or any combination thereof.

The compositions may be formulated according to any of the conventional methods known in the art and widely described in the literature. Thus, the active ingredient may be incorporated, optionally together with other active substances, with one or more conventional carriers, diluents and/or excipients, to produce conventional galenic preparations such as tablets, pills, powders, lozenges, sachets, cachets, elixirs, suspensions, emulsions, solutions, syrups, aerosols (as a solid or in a liquid medium), soft and hard gelatin capsules, sterile injectable solutions sterile packaged powders, and the like.

Examples of suitable carriers, excipients, and diluents are lactose, dextrose, sucrose, sorbitol, mannitol, starches, gum acacia, calcium phosphate, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, and the like.

Preferably, the pharmaceutical composition is in enteric-coated form, e.g. to protect it from the acidic environment of the stomach.

In one embodiment, the pharmaceutical composition comprises one or more compounds of the present invention together with one or more compounds which are known in the art to inhibit lipase, to bind fat and/or to inhibit the glucose transporter. Examples of suitable compounds which could be mixed with the compounds of the present, inventions include but are not limited to those described in U.S. Pat. Nos. 6,235,305, 6,267,952, 6,534,087 and 6,756,364 (lipase inhibitors) and U.S. Pat. No. 6,264,937 (fat-binding polymers). The effects of the compounds present in such mixtures may complement each other, or there may be an synergistic effect.

Non pharmaceutical compositions are also envisaged but similar carriers, diluents or excipients may be used. Moreover the compositions may be in the form of a drink or a solid foodstuff. For example, soluble compounds of the invention may be formulated in a drink while insoluble compounds are formulated in a solid food, e.g. bar, cake, chocolate etc. Thus additional ingredients may include water, protein, fibre, fats and/or carbohydrates. Thus the compositions may typically contain a compound of the invention and one or more nutritional (e.g. calorific) components normally found in foodstuffs and drinks.

Further, the invention provides a kit comprising
(a) one or more compounds of the present invention and;
(b) one or more compounds which are known in the art to inhibit lipase, to bind fat and/or to inhibit SGLT, as a combined preparation for separate, simultaneous or sequential administration to a patient, e.g. for aiding weight loss or inhibiting weight gain or to treat diabetes (Type 1 or Type 2) or Metabolic Syndrome or related disorders.

In a further aspect, the present invention provides a method of medical treatment comprising administration of a therapeutically effective amount of a compound of the invention as defined above to a subject in need thereof.

Subjects in need of medical treatment according to the present invention include those which are overweight or obese. Body Mass Index (BMI) may be used to determine whether a patient is overweight. BMI is calculated by dividing a person's body weight in kilograms by their height in meters squared. Generally, a BMI of 30 or more is considered obese and a BMI between 25 to 29.9 is considered overweight. The subject will therefore typically have a BMI of at least 25, preferably of at least 30.

Alternatively or in addition, the absolute waist circumference and/or the waist-hip ratio may be used as measures of central obesity. A male subject will preferably have a waist circumference of at least 102 cm and/or a waist-hip ratio of at least 0.9. A female subject will preferably have a waist circumference of at least 88 cm and/or a waist-hip ratio of at least 0.85.

Typically, men with more than 25% body fat and women with more than 30% body fat are obese, so the subject will preferably have at least 25% body fat if he is male and at least 30% body fat if she is female.

In a further embodiment the compounds of the present invention are used to prevent weight gain and/or to help weight loss in a subject who is not clinically overweight or obese. In this embodiment the subject will typically have a BMI of between 18 and 24.9 and/or a waist circumference of less than 102 cm (males) or 88 cm (females) and/or a waist-hip ratio of less than 0.9 (males) or 0.85 (females) and/or have less than 30% (males) or less than 25% (females) body fat.

The skilled person will be able to determine suitable effective amounts without undue experimentation. Examples of preferred suitable amounts are at least 1 mg/Kg body weight of the subject, e.g. about 5 mg/Kg body weight of the subject, preferably about 10, 15 or 20 mg/Kg body weight. Suitable dosage ranges therefore include 1-20 mg/Kg body weight, preferably 2-10 mg/Kg body weight. These may be daily, pre-prandial or one off dosages. It will be appreciated that suitable dosages may depend on the type and frequency of administration, e.g. smaller dosages will be appropriate if the compound is administered both before and during food intake. Smaller dosages will also be appropriate when administered with lipase inhibitors such as tetrahydrolipstatin.

In a preferred embodiment, the compounds of the present invention are used to prevent weight gain and/or to aid weight loss. The compounds of the invention may be used to inhibit glucose absorption and/or triglyceride metabolism, in particular to inhibit the SGLT transporter and/or lipase, in particular gastric or pancreatic lipase.

In a further aspect, the present invention provides a compound of the invention as defined above for use in therapy, in particular for use in preventing weight gain and/or aiding weight loss, preferably to inhibit glucose absorption and/or triglyceride metabolism, in particular to inhibit the SGLT transporter and/or lipase.

In a further aspect, the present invention provides the use of a compound of the invention as defined above in the manufacture of a medicament for the treatment of a condition as defined below.

The conditions which can be treated or prevented according to the invention, and utilising the compounds of the invention as described above, include any conditions which benefit from reduced glucose absorption in the intestine and/or reduced dietary triglyceride metabolism. Examples of such conditions include obesity, hyperlipaemia, diabetes, especially type II diabetes but also type I, as well as hyperglycemia, hyperinsulinemia, hypertriglyceridemia, Metabolic Syndrome, dumping syndrome, atherosclerosis and related diseases.

The compounds of the present invention may also be used for non-therapeutic applications, e.g. to help weight loss and/or to prevent weight gain for cosmetic purposes. Thus, nutritional supplements comprising one or more compounds of the present invention for use in a method of controlling weight are a further aspect of the present invention.

In a preferred embodiment, the compounds of the present invention are administered at a time point which is a suitable period of time before food intake. This may allow the compounds of the present invention to access and block the SGLT transporter and to inhibit lipase before the dietary glucose and triglycerides enters the intestine, thus decreasing the chances of any glucose being able to interact with the transporter and the chances of any triglyceride of interacting with lipase. Suitable time periods are preferably at least 10, e.g. 20 minutes before food intake, more preferably 30 minutes, but longer periods of e.g. 1 hour or 2 hours may also be suitable. In another embodiment, any food and the compounds of the present invention are consumed substantially simultaneously. In yet another embodiment, the compounds of the present invention are administered after food intake. In yet another embodiment, the compounds of the present invention are administered at various time points, e.g. before and during food consumption. This latter embodiment may be particularly suitable if the formulation is a drink which a subject chooses to accompany a meal as with any other standard beverage, e.g. soft drink, alcoholic drink, tea, coffee, etc.

Administration is typically oral, although other methods of delivery, e.g. gavage or injection into the intestine are also contemplated.

The subject is preferably a mammal, most preferably a human subject.

The present invention will be further described in the following non-limiting Examples and with reference to the Figures in which.

EXAMPLES

Abbreviations

Figure 1:
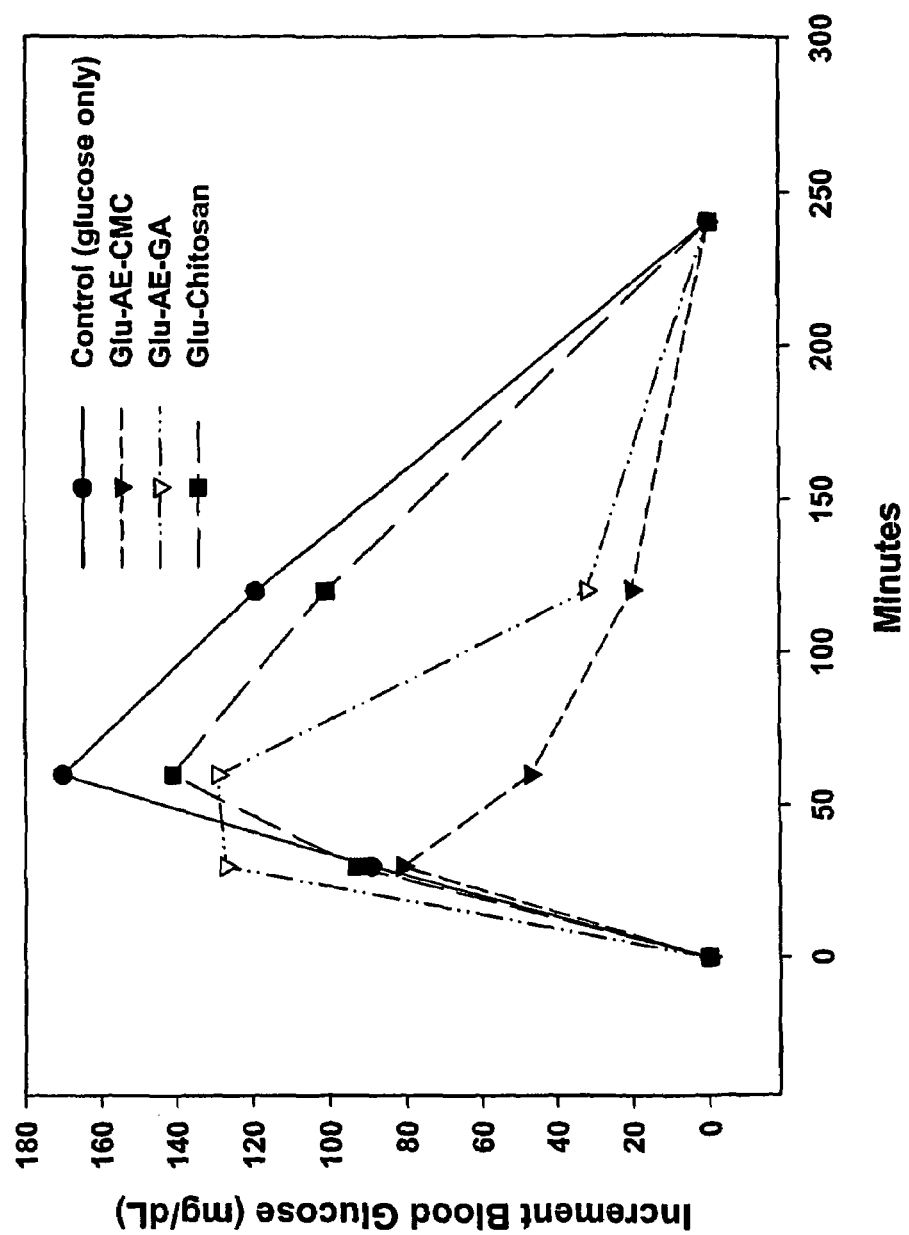
FIG. 1 is a graph showing the effect of selected compounds of the present invention on glucose absorption in a human subject. The Experiment was carried out as described in Example 8.1.

AE—Aminoethyl
AEC—aminoethylcarboxymethyl
AES—Aminoethane sulfonic acid
CMC—Carboxymethylcellulose
Dex—Dextran
EDA—Ethylenediamine
EDC—1-Ethyl-3-(3-dimethylaminopropyl)carbodiimide
EH—2-Ethylhexylamine
GA—Gum Arabic Glu—glucose
Gal—galactopyranosyl
LP—low methyl pectin
PA—polyallylamine
PEI—polyethyleneimine
TEAE—Tris(2-aminoethyl)amine
DAD—Diaminodecane
TMA—Trimethylolpropane tris[poly(propylene glycol) amine terminated]ether Example 1

Preparation of Substituted Polymers 1.1 Preparation of glucopyranosyl-aminoethylated carboxymethylcellulose (Glu-AE-CMC)
1. 5 g of Carboxymethylcellulose (CMC) sodium salt dissolved in 200 mL of deionized H2O.
2. 93 g of Ethylenediamine dihydrochloride (EDA) was added to the CMC solution and the pH adjusted to 4.7 with 1N NaOH.
3. 6.7 g of 1-Ethyl-3-(3-dimethylaminopropyl)carbodiimide hydrochloride (EDC) was added to the solution and the pH was maintained at 4.7 with 1N HCl for 3 hours.
4. The preparation was dialyzed extensively against deionized H2O and lyophilized.
5. 2 g of AE-CMC dissolved in 200 mL of deionized H2O.
6. 3 g of glucuronic acid dissolved in the AE-CMC solution. The pH adjusted with 10N NaOH to 4.7.
7. 6 g of EDC added to the solution and pH was maintained at 4.7 by addition of 1N HCl. The reaction proceeded for 3 hours.
8. The solution was dialyzed extensively against deionized H2O followed by lyophilization.

1.2 Preparation of Tris-aminoethylated Carboxymethylcellulose (TAEA-CMC)
1. 1 g CMC dissolved in 100 mL of deionized H2O.
2. 5 mL of 6.7M Tris(2-aminoethyl)amine was added and the pH adjusted to 4.7 with 10N HCl
3. 1.34 g of EDC was used for coupling the reaction and the pH maintained at 4.7 by addition of 1N HCl for 3 hours
4. The TAEA-CMC preparation was exhaustively dialyzed against deionized H2O followed by lyophilization.

1.3 Preparation of Aminoethane Sulfonated Carboxymethylcellulose (AES-CMC)
1. 0.5 g CMC dissolved in 50 mL of deionized H2O.
2. 1 g Aminoethane sulfonic acid was added to the CMC solution and pH adjusted to 4.7.
3. 0.67 g of EDC was used for coupling the reaction and the pH maintained at 4.7 by addition of 1N HCl for 3 hours.
4. The AES-CMC preparation was exhaustively dialyzed against deionized H2O followed by lyophilization.

1.4 Preparation of Ethylhexylamine conjugate of Carboxymethylcellulose (EH-CMC)
1. 0.5 g CMC dissolved in 50 mL of deionized H2O.
2. 0.6 g of 2-Ethylhexylamine-HCl added and the solution pH was adjusted to 4.7 with 0.1N HCl
3. 0.8 g of EDC was added and pH maintained at 4.7 for 30 min.
4. Because of the excess foaming generate the reaction was terminated by 200 ul of 5M EDA, the detergent-like solution was dialyzed extensively against deionized H2O and maintained in solution.

1.5 Preparation of Glucamine Conjugate of Carboxymethylcellulose (Glucamine-CMC)
1. 0.5 g CMC dissolved in 50 mL of deionized H2O.
2. 0.5 g of D-glucamine added and the solution pH was adjusted to 4.7 with 0.1N HCl
3. 0.67 g of EDC was added and pH maintained at 4.7 for 3 hours.
4. The solution glucamine-CMC conjugate was dialyzed extensively against deionized H2O and lyophilized.

1.6 Preparation of Glucosamine Conjugate of Carboxymethylcellulose (Glucosamine-CMC)
1. 0.5 g CMC dissolved in 50 mL of deionized H2O.
2. 0.5 g of D-glucosamine HCl added and the solution pH was adjusted to 4.7 with 1N NaOH
3. 0.67 g of EDC was added and pH maintained at 4.7 for 3 hours.
4. The solution glucosamine-CMC conjugate was dialyzed extensively against deionized H2O and lyophilized.

1.7 Preparation of Glucopyranosyl-chitosan (Glu-chitosan)
1. 1.0 g chitosan was added to 100 mL of deionized H2O acidified with 2 mL of 10N HCl. The mixture was stirred overnight to allow chitosan to go into solution.
2. 1.5 g of glucuronic acid dissolved in 25 mL of deionized H2O added and the solution pH was adjusted to 4.7 with 2N NaOH
3. 2.0 g of EDC added and pH maintained at 4.7 for 3 hours.
4. The solution Glu-chitosan conjugate was dialyzed extensively against deionized H2O and maintained in solution.

1.8 Preparation of Glucopyranosyl-AECM-Ficoll (Glu-AECM-Ficoll)
1. 5 g of Ficoll 400 was dissolved in 70 mL of 1.35 M Chloroacetic acid
2. 13.5 mL 10N NaOH and 5 mL of H2O were added and the reaction allowed to proceed overnight at 40° C.
3. The reaction was terminated by addition of 3.75 mL of 2 M NaH2PO4 and neutralized with 5N HCl.
4. The CM-Ficoll was dialyzed extensively against deionized H2O and lyophilized.
5. The lyophilized CM-Ficoll was dissolved in dissolved in 200 mL deionized H2O.
6. 93 g of EDA was added to the CM-Ficoll solution and the pH adjusted to 4.7 with 1N NaOH.
7. 6.7 g of EDC was added to the solution and the pH was maintained at 4.7 with 1N HCl for 3 hours.
8. The preparation AECM-FiColl was dialyzed extensively against deionized H2O and lyophilized.
9. 2 g of AECM-Ficoll was dissolved in 100 mL of deionized H2O.
10. 3 g of glucuronic acid dissolved in the AECM-Ficoll solution. The pH adjusted with 10N NaOH to 4.7.
11. 6 g of EDC added to the solution and pH was maintained at 4.7 by addition of 1N HCl. The reaction proceeded for 3 hours.
12. The preparation Glu-AECM-Ficoll was dialyzed extensively against deionized H2O followed by lyophilization.

1.9 Preparation of Galactopyranosyl-AECM-FiColl (Gal-AECM-Ficoll)
1. 5 g of Ficoll 400 was dissolved in 70 mL of 1.35 M Chloroacetic acid
2. 13.5 mL 10N NaOH and 5 mL of H2O were added and the reaction allowed to proceed overnight at 40° C.
3. The reaction was terminated by addition of 3.75 mL of 2 M NaH2PO4 and neutralized with 5N HCl.
4. The CM-Ficoll was dialyzed extensively against deionized H2O and lyophilized.
5. The lyophilized CM-Ficoll was dissolved in 200 mL deionized H2O.

6. 93 g of EDA was added to the CM-Ficoll solution and the pH adjusted to 4.7 with 1N NaOH.
7. 6.7 g of EDC was added to the solution and the pH was maintained at 4.7 with 1N HCl for 3 hours.
8. The preparation AECM-Ficoll was dialyzed extensively against deionized H2O and lyophilized.
9. 2 g of AECM-Ficoll was dissolved in 100 mL of deionized H2O.
10. 3 g of D-galacturonic acid dissolved in the AECM-Ficoll solution. The pH adjusted with 10N NaOH to 4.7.
11. 6 g of EDC added to the solution and pH was maintained at 4.7 by addition of 1N HCl. The reaction proceeded for 3 hours.

The preparation Gal-AECM-Ficoll was dialyzed extensively against deionized H2O followed by lyophilization.

1.10 Preparation of Glucopyranosyl-AECM-Dextran (Glu-AECM-Dextran)
1. 5 g of Dextran (MW 5×106-40×106) was dissolved in 140 mL of 1.35 M Chloroacetic acid
2. 27 mL 10N NaOH and 10 mL of H2O were added and the reaction allowed to proceed overnight at 40° C.
3. The reaction was terminated by addition of 7.5 mL of 2 M NaH2PO4 and neutralized with 5N HCl.
4. The CM-Dextran was dialyzed extensively against deionized H2O and lyophilized.
5. The lyophilized CM-Dextran was dissolved in 200 mL deionized H2O.
6. 93 g of EDA was added to the CM-Dextran solution and the pH adjusted to 4.7 with 1N NaOH.
7. 6.7 g of EDC was added to the solution and the pH was maintained at 4.7 with 1N HCl for 3 hours.
8. The preparation AECM-Dextran was dialyzed extensively against deionized H2O and lyophilized.
9. 2 g of AECM-Dextran was dissolved in 100 mL of deionized H2O.
10. 3 g of glucuronic acid dissolved in the AECM-Dextran solution. The pH adjusted with 10N NaOH to 4.7.
11. 6 g of EDC added to the solution and pH was maintained at 4.7 by addition of 1N HCl. The reaction proceeded for 3 hours.
12. The preparation Glu-AECM-Dextran was dialyzed extensively against deionized H2O followed by lyophilization.

1.11 Preparation of Glucopyranosyl-DEAE-Dextran (Glu-DEAE-Dex)
1. 0.5 g DEAE-Dextran (purchased from Sigma-Aldrich) dissolved in 200 mL of deionized H2O.
2. 0.3 g glucuronic acid added to the DEAE-Dex and pH adjusted to 4.7 with 2N NaOH.
3. 0.6 g EDC added to the solution and pH was maintained at 4.7 for 3 hours with 0.1N HCl
4. The Glu-DEAE-Dex solution was extensively dialyzed and lyophilized.

1.12 Dextran-sulfate
This was purchased from Aldrich-Sigma.

1.13 Preparation of Glucopyranosyl-aminoethylated Gum Arabic (Glu-AE-GA)
1. 5 g Gum Arabic dissolved in 100 mL of deionized H2O.
2. 6.6 g of sodium periodate was added to the GA solution and pH adjusted to 5.0 with 2N NaOH.
3. The reaction was covered with foil and stirred for 24 hours at 40° C.
4. The dialdehyde GA was dialyzed exhaustively against water.
5. 25 g of EDA was added to the solution followed by the addition of 2.5 g sodium cyanoborohydride dissolved in 10 mL of dimethylformamide and 15 mL of 1N NaOH. The reaction mixture was stirred overnight at room temperature.
6. After extensive dialysis the resulting aminoethylated GA (AE-GA) was lyophilized.
7. 2 g of AE-GA dissolved in 60 mL deionized H2O followed by addition of 2 g glucuronic acid in 20 mL deionized H2O. The pH adjusted with 2.5N NaOH to 4.7.
8. 4 g of EDC was added to the solution and the pH was maintained at 4.7 with 1N HCl for 3 hours.
9. The Glu-AE-GA preparation was dialyzed against deionized H2O and lyophilized.

1.14 Preparation of Tris-aminoethylated Gum Arabic (TAEA-GA)
1. 0.5 g Gum Arabic dissolved in 50 mL of deionized H2O.
2. 2 mL of 6.7M Tris(2-aminoethyl)amine was added and the pH adjusted to 4.7 with 10N HCl
3. 0.67 g of EDC was used for coupling the reaction and the pH maintained at 4.7 by addition of 1N HCl for 3 hours
4. The TAEA-GA preparation was exhaustively dialyzed against deionized H2O followed by lyophilization.

1.15 Preparation of Aminoethane sulfonated Gum Arabic (AES-GA)
1. 0.5 g Gum Arabic dissolved in 50 mL of deionized H2O.
2. 1 g Aminoethane sulfonic acid was added to the GA solution and pH adjusted to 4.7.
3. 0.67 g of EDC was used for coupling the reaction and the pH maintained at 4.7 by addition of 1N HCl for 3 hours.
4. The AES-GA preparation was exhaustively dialyzed against deionized H2O followed by lyophilization.

1.16 Preparation of Ethylhexylamine Conjugate of Gum Arabic (EH-GA)
1. 0.5 g Gum Arabic dissolved in 50 mL of deionized H2O.
2. 0.35 g of 2-Ethylhexylamine-HCl added and the solution pH was adjusted to 4.7 with 0.1N HCl
3. 0.75 g of EDC was added and pH maintained at 4.7 for 3 hours.
4. The EH-GA, detergent-like solution, was dialyzed extensively against deionized H2O and lyophilized.

1.17 Preparation of Tris-aminoethylated Low Methylation pectin (TAEA-LMP)
1. 0.5 g LMP mixed with 2.5 g sucrose before adding the mixture slowly with vigorous stirring into 50 mL of deionized H2O.
2. 2 mL of 6.7M Tris(2-aminoethyl)amine was added and the pH adjusted to 4.7 with 10N HCl
3. 0.67 g of EDC was used for coupling the reaction and the pH maintained at 4.7 by addition of 1N HCl for 3 hours
4. The TAEA-LMP preparation was exhaustively dialyzed against deionized H2O.

1.18 Preparation of Aminoethyl Alginate (EA-Alginate)
1. 0.5 g sodium alginate dissolved by vigorous stirring in 50 mL of deionized H2O.
2. 9.3 g of EDA added to the solution while maintaining the pH at 6.0 with 1N NaOH
3. 0.67 g of EDC was used for coupling the reaction and the pH maintained at 6.0 by addition of 0.1N HCl for 3 hours
4. The EA-alginate preparation was exhaustively dialyzed against deionized H2O.

1.19 Preparation of Glucopyranosyl Trimethylolpropane tris [poly(propylene glycol)amine Terminated] Carboxymethyl-cellulose (Glu-TMA-CMC)
1. 14 g CMC dissolved in 448 mL of deionized H2O and pH adjusted to 5.0.

2. 112 mL of Trimethylolpropane tris[poly(propylene glycol)amine terminated]ether was diluted with an equal volume of H2O and the pH adjusted to 5.2 with 10N HCl
3. 14 g of EDC was used for coupling the reaction and the pH maintained at 4.7 by addition of 1N HCl for 3 hours
4. The TMA-CMC preparation was exhaustively dialyzed against deionized $H_2O$ followed by the reduction of volume to 400 mL by partial lyophilization.
5. 10 g glucuronic acid was added to the TMA-CMC solution and pH adjusted to 5.0 with 10N NaOH.
6. 10 g EDC added to the solution and pH was maintained at 4.7 by addition of 1N HCl. The reaction proceeded for 3 hours.
7. The solution was dialyzed extensively against deionized $H_2O$ and lyophilized.

1.20 Preparation of Galactopyranosyl-AE-CMC (Gal-AE-CMC)
1. 180 mg of AE-CMC dissolved in 5 mL of deionized $H_2O$.
2. 358 mg of lactobionic acid was dissolved in 4 mL of deionized $H_2O$ and added to the AE-CMC solution and the pH adjusted to 4.7 with 1N NaOH.
3. 191 mg of EDC was added to the lactobionic acid AE-CMC solution and the reaction pH was maintained at 4.7 by addition of 0.1N HCl for 3 hours.
4. The preparation was dialyzed extensively against deionized $H_2O$.

1.21 Preparation of Galactopyranosyl-TMA-CMC (Gal-TMA-CMC)
1. 100 mg of TMA-CMC dissolved in 15 mL of deionized $H_2O$.
2. 148 mg of lactobionic acid was dissolved in 1.5 mL of deionized $H_2O$ and added to the TMA-CMC solution and the pH adjusted to 4.7 with 1N NaOH.
3. 148 mg of EDC was added to the lactobionic acid TMA-CMC solution and the reaction pH was maintained at 4.7 by addition of 0.1N HCl for 3 hours.
4. The preparation was dialyzed extensively against deionized $H_2O$.

1.22 Preparation of Glucopyranosyl Diaminodecane Arabic Gum (Glu-DAD-GA)
1. 1 g Gum Arabic dissolved in 20 mL of deionized $H_2O$.
2. 1 g of 1,10-diaminodecane (DAD) dissolved in 6 mL of methanol.
3. The DAD and GA solutions were mixed and pH adjusted to 4.7 using 10N HCl.
4. 1 g of EDC was added to the solution and the pH was maintained at 4.7 with 1N HCl for 3 hours.
5. The DAD-GA preparation was dialyzed extensively against deionized $H_2O$ and lyophilized.
6. The DAD-GA was dissolved in 100 mL of deionized $H_2O$.
7. 0.5 g of glucuronic acid was added to the DAD-GA solution and the pH adjusted to 4.7.
8. 0.5 g of EDC added to the solution and pH was maintained at 4.7 by addition of 1N HCl. The reaction proceeded for 3 hours.
9. The solution was dialyzed extensively against deionized $H_2O$.

1.23 Preparation of Glucopyranosyl Trimethylolpropane tris [poly(propylene glycol)amine Terminated] Gum Arabic (Glu-TMA-GA)
1. 0.5 g GA dissolved in 8 mL of deionized H2O and pH adjusted to 5.
2. 5 mL of Trimethylolpropane tris[poly(propylene glycol) amine terminated]ether was diluted with an equal volume of $H_2O$ and the pH adjusted to 5.2 with 10N HCl
3. 0.5 g of EDC was used for coupling the reaction and the pH maintained at 4.7 by addition of 1N HCl for 3 hours
4. The TMA-GA preparation was exhaustively dialyzed against deionized H2O followed by lyophilization.
5. 210 mg glucuronic acid was added to 40 mL of TMA-GA solution and pH adjusted to 4.6 with 10N NaOH.
6. 200 mg EDC added to the solution and pH was maintained at 4.7 by addition of 1N HCl. The reaction proceeded for 3 hours.
7. The solution was dialyzed extensively against deionized $H_2O$ and lyophilized.

1.24 Preparation of Galactopyranosyl-polyallylamine (Gal-PA)
1. 200 mg of polyallylamine hydrochloride dissolved in 4 mL of deionized $H_2O$. The pH was adjusted to 4.7 with 1N NaOH;
2. 200 mg of lactobionic acid was added to and dissolved in the PA solution and the pH adjusted to 4.7 with 1N NaOH.
3. 250 mg of EDC was added to the lactobionic acid PA solution and the reaction pH was maintained at 4.7 by addition of 0.1N HCl for 3 hours.
4. The preparation was dialyzed extensively against deionized $H_2O$.

Example 2

Lipase Inhibition Assay

Lipase activity was assayed using two different standard assay methods, which are known in the art.

2.1 Tributyrin Colormetric Assay

This assay was carried out according to the method described by Choi S J, Hwang J M, Kim S I. A calorimetric microplate assay method for high throughput analysis of lipase activity. J Biochem Mol Biol. 2003 Jul. 31; 36(4):417-20.

The standard assay method involved the following steps:
1. 5,5'-dithiobis(2-nitro benzoic acid) (DTNB) stock solution (40 mM) was prepared in isobutanol.
2. 2,3-dimercapto-1-propanol tributyrate (DMPTB) (10 mM) was dissolved in 6% Triton X-100, 50 mM Tris-Cl, pH 7.2.
3. The two stock solutions were stored at −20° C.
4. Porcine pancreatic lipase (Worthington, N.J., USA) was dissolved in or diluted with buffer L (10 mM KCl, 10 mM Tris-Cl, pH 7.5).
5. The standard reaction mixture contained 0.2 mM DMPTB, 0.8 mM DTNB, 1 mM EDTA, 0.05% Triton X-100, and 50 mM Tris-Cl, pH 7.5.
6. For the preparation of the standard reaction mixture, 20 µl of 10 mM DMPTB, 20 µl of 40 mM DTNB, 2 µl of 0.5M EDTA, 5 µl of 10% Triton X-100, and 50 µl of 1 M Tris-Cl, pH 7.5 were mixed in a microcentrifuge tube and 803 µl of deionized water was added to make a final volume of 900 µl.
7. Microplate wells were filled with 180 µl of this mixture and 20 µl of the enzyme sample (test material) was added to each well.
8. The microplate was immediately transferred to a 37° C. incubator to start the reaction.
9. After the indicated 30 min period of incubation, the absorbance of each well at 405 nm was measured using STAT FAX 2100 microplate reader.

2.2 1,2-Diglyceride Hydrolysis

This was measured by using a commercially available Lipase-PS™ kit (Trinity Biotech Plc, IDA Business Park, Bray, Co Wicklow, Ireland.) according to the manufacturer's instructions.

Example 3

Inhibition of Lipase by Chiotosan and Chitosan-Glu

Chitosan-Glu was prepared according to the method of Example 1.7 and lipase inhibition was measured using the methods described in Example 2. The results are shown in Table 1.

Chitosan is known in the art to have some lipase inhibitory activity. However, the present inventors have surprisingly found that conjugation of a glucopyranosyl moiety to chitosan yields a compound with much greater inhibitory properties. Chitosan-Glu was found to have a significantly increased inhibitory effect on pancreatic lipase, even when used at lower concentrations than unmodified Chitosan.

TABLE 1

Lipase inhibition by Chitosan and substituted Chitosan

|  | Conc (µg/mL) | Tributyrin | Diglyceride |
|---|---|---|---|
| Chitosan | 1000 | 31 | 0 |
| Chitosan-Glu | 830 | 56 | 35 |

Lipase inhibition is shown in %

Example 4

Lipase Inhibition by Ficoll Conjugates

Ficoll was conjugated with amino-ethyl-carboxy-methyl as described in steps 1-4 of Example 1.8. Glucopyranosyl-AECM-Ficoll was prepared as described in Example 1.8. Galactopyranosyl-AECM-Ficoll was prepared as described in Example 1.9. Lipase inhibition was measured as described in Example 2. The results are shown in Table 2 which shows that all of the compounds tested had good lipase inhibitory properties.

TABLE 2

Lipase inhibition by Ficoll conjugates

|  | Conc. (µg/mL) | Tributyrin |
|---|---|---|
| Ficoll-AECM | 125 | 59 |
| Ficoll-AECM-Glu | 125 | 47 |
| Ficoll-AECM-Gel | 125 | 55 |

Lipase inhibition is shown in %

Example 5

Lipase Inhibition by Gum Arabic Conjugates

Various Gum Arabic conjugates were prepared as described in Example 1 and lipase inhibition was measured as described in Example 2. The results are shown in Table 3. Unmodified Gum Arabic does not have any lipase-inhibitory function. On the contrary, it appears to enhance lipase activity. As can be seen from Table 3, conjugation with a glucopyramidyl moiety yielded the most efficient lipase inhibitor.

TABLE 3

Lipase inhibition by Gum Arabic and conjugates thereof

|  | Conc. (µg/mL) | Tributyrin | Diglyceride |
|---|---|---|---|
| GA | 125 | (−45) |  |
| Glu-AE-GA | 125 | 67 | 12 |
| EH-GA | 125 | 69 | (−39) |
| AE-GA | 125 | 21 | 0 |
| TAEA-GA | 125 | 56 |  |
| AES-GA | 250 | 33 |  |

Lipase inhibition is shown in %.

Example 6

Lipase Inhibition by Dextran Conjugates

Dextran conjugates were prepared as described in Example 1 and lipase inhibition was measured as described in Example 2. The results are shown in Table 4. It can be seen that the most significant inhibition of lipase activity is achieved with the Dextran-DEAE-Glu conjugate. The tributyrin assay shows reasonably good inhibition by Dextran sulfate, but no inhibition of diglyceride was observed. In a separate experiment, increasing Dextran sulfate concentrations were tested, with a maximum of 1000 µg/mL, but this did not cause any increase in inhibition as measured by the tributyrin assay.

TABLE 4

Lipase inhibition by Dextran conjugates

|  | Conc. (µg/mL) | Tributyrin | Diglyceride |
|---|---|---|---|
| Dextran | 2000 | 0 | 0 |
| DEAE-Dex | 31 | 52 | 56 |
| Glu-DEAE-Dex | 31 | 61 | 98 |
| Dex-sulfate | 10 | 46 | 0 |

Lipase inhibition is shown in %

Example 7

Lipase Inhibition by Carboxymethylcellulose Conjugates

Carboxymethylcellulose conjugates were prepared as described in Example 1 and lipase inhibition was measured as described in Example 2. The results are shown in Table 5. The inhibitory activity of the Glu-EA-CMC was highest, achieving essentially the same percentage inhibition at a concentration of only 125 µg/mL as AE-CMC and TAEA-CMC at a concentration of 625 µg/mL, i.e. 5 times higher.

TABLE 5

Lipase inhibition by Carboxymethylcellulose conjugates

|  | Conc. (µg/mL) | Tributyrin | Diglyceride |
|---|---|---|---|
| AE-CMC | 10,000 | 0 |  |
| Glu-AE-CMC | 125 | 59 | 30 |
| CMC | 625 | 60 |  |
| TAEA-CMC | 625 | 56 |  |
| EH-CMC | 125 | (−40) |  |

Lipase inhibition is shown in %

Example 8

Inhibition of Glucose Transport 8.1 Oral Glucose Transport Test in Human Subject
1. Subject fasted overnight (10-14 hours)
2. 1 g of the test material (Glu-AE-CMC, Glu-AE-GA, or Glu-Chitosan) was consumed 30-45 min prior to glucose challenge.
3. Baseline blood glucose level was determined using Bayer Ascensia microlet for blood sampling into Bayer Ascensia Microfill blood glucose test strip and Bayer Ascensia Contour glucometer.
4. 70 g of glucose prepared in 250 ml water was used for challenge. The challenge involved oral consumption of the glucose.
5. Blood was sampled at 10 min, 30 min, and 1, 2, and 4 hours after glucose challenge.
6. Increment of blood glucose determined by subtracting the baseline blood glucose value from those sampled at different intervals.

The results are shown in FIG. 1. The area under the curve was determined by using SigmaPlot 8.0 graphics program and the data is summarised in Table 6.

TABLE 6

Inhibition of glucose transport

|  | Area under curve | Inhibition |
|---|---|---|
| Glucose | 13890 | NA |
| Glu-AE-GA | 10575 | 23.4% |
| Glu-Chitosan | 12165 | 12.4% |
| Glu-AE-CMC | 5145 | 63% |

NA = not applicable 8.2 Oral Glucose Tolerance Test (Mouse)
1. Mice were kept without food for 2 hours prior to testing
2. Each mouse weight was determined.
3. The test material in 250 µl was pre-loaded by intragastric gavage into each mouse 30 min prior to glucose challenge.
4. Prior to glucose challenge, baseline blood glucose level was determined using micropipette for blood sampling from the retro-orbital venous plexus into Bayer Ascensia Microfill blood glucose test strip and Bayer Ascensia Contour glucometer.
5. 100 mg/mL of glucose prepared. The volume administered was adjusted to weight at 10 µl of glucose solution/g of body weight.
6. Blood was sampled at 10 min, 30 min, and 60 min after glucose challenge.
7. Increment of blood glucose determined by subtracting the baseline blood glucose value from those sampled at different intervals.

Figure 2:
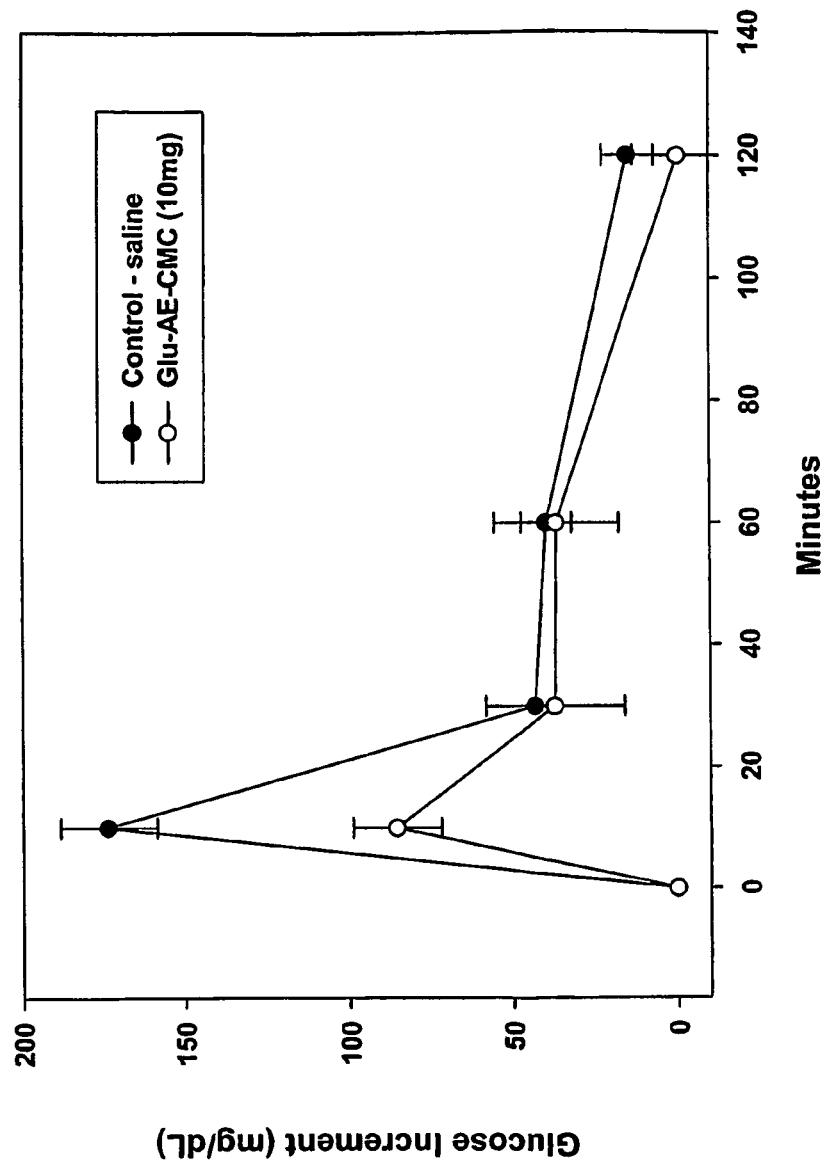
FIG. 2 is a graph showing the effect of CMC-AE-Glu on glucose absorption in mice. The Experiment was carried out as described in Example 8.2.

The results are shown in FIG. 2. The area under the curve was determined by using SigmaPlot 8.0 graphics program and the data is summarised in Table 7.

TABLE 7

Inhibition of glucose transport in mice

| Polymer-Conjugate | Dose | Inhibition |
|---|---|---|
| CMC | 10 mg | No |
| Glu-AE-CMC | 10 mg | 35% |
| Glu-AECM-Dextran | 7.5 mg | 37% |
| DEAE-Dextran | 10 mg | No |
| Glu-AECM-Ficoll | 7.5 mg | 32% |
| Glucosamine-CMC | 10 mg | No |
| Glucamine-CMC | 10 mg | No |
| Glucosamine-CM-Dextran | 10 mg | No |

8.3 Oral Glucose Transport Test in Human Subject

This test was essentially carried out as described in Example 8.1, but the test material included Glu-PA and Glu-DAD-GA with glucose serving as a control. Blood sampling was ceased after 2 hours.

Figure 4:
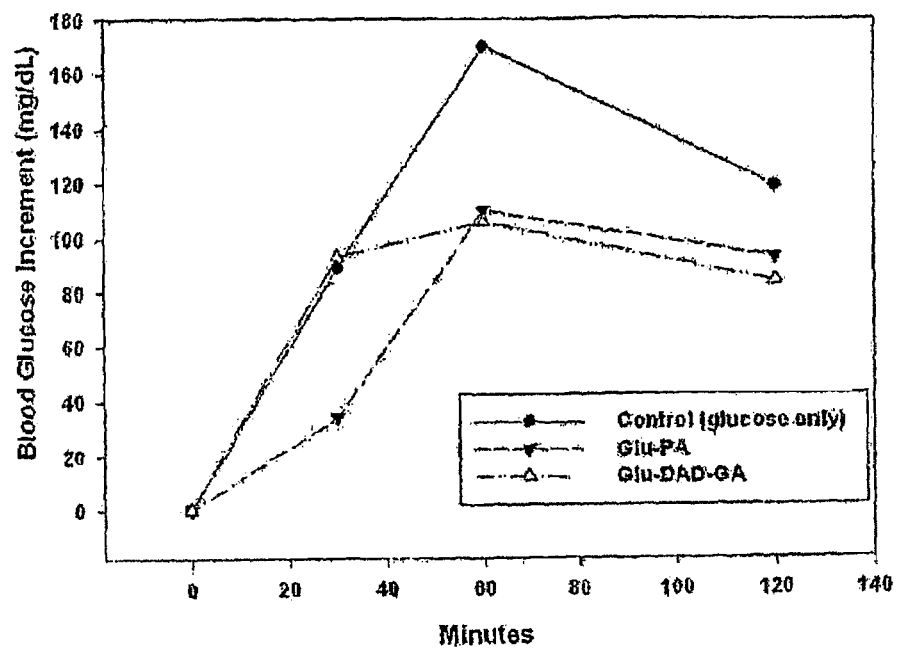
FIG. 4 is a graph showing the effect of various Glu-polymer conjugates on glucose absorption in a human subject. The Experiment was carried out as described in Example 8.3.

The results are shown in FIG. 4. The area under the curve was determined using SigmaPlot 8.0 graphics program and the data is summarised in Table 9.

TABLE 9

Inhibition of glucose transport -human glucose absorption inhibition at 2 hours

| Polymer-Conjugate | AUC | Inhibition |
|---|---|---|
| Glucose | 13890 | NA |
| Glu-PA | 8760 | 37% |
| Glu-DAD-GA | 10080 | 27% |

NA = not applicable

Example 9

Preparation of Glucopyranosyl-polyallylamine (Glu-PA)

1. 100 mg of polyallylamine hydrochloride dissolved in 1 mL of deionized $H_2O$. The pH was adjusted to 4.7 with 1N NaOH.
2. 184 mg of glucuronic acid dissolved in 1.2 ml of deionized $H_2O$ and the pH adjusted to 4.7 with 1N NaOH.
3. 180 mg of 1-Ethyl-3-(3-dimethylaminopropyl) carbodiimide hydrochloride (EDC) was added to the glucuronic solution and the solution was immediately transferred drop-wise to the PA solution.
4. The reaction pH was maintained at 4.7 by addition of 0.1N NaOH for 3 hours.
5. The preparation was dialyzed extensively against deionized $H_2O$.

Example 10

Preparation of Glucopyranosyl-polyethyleneimine (Glu-PEI)

1. 100 mg of PEI (0.35 ml of 30% water solution) was added to 2.7 ml of 1N HCl. The pH was adjusted to 4.7.
2. 200 mg of glucuronic acid dissolved in 1.2 ml of deionized $H_2O$ and the pH adjusted to 4.7 with 1N NaOH.
3. 185 mg of 1-Ethyl-3-(3-dimethylaminopropyl)carbodiimide hydrochloride (EDC) was added to the glucuronic solution and the solution was immediately transferred to the PEI solution by drop-wise addition.
4. The reaction pH was maintained at 4.7 by addition of 0.1N NaOH for 3 hours.
5. The preparation was dialyzed extensively against deionized $H_2O$.

Example 11

Lipase and Glucose Transport Inhibition by Glu-PA and Glu-PEI

Lipase inhibition was measured as described in Example 2 and the results of this experiment are shown Table 8 below.

TABLE 8

Lipase inhibition by Glu-PA and Glu-PEI

| | Conc. (•g/mL) | Tributyrin | Diglyceride |
|---|---|---|---|
| PA | 31 | 45 | 35 |
| Glu-PA | 31 | 39 | 33 |
| PEI | 31 | 7 | 0 |
| Glu-PEI | 31 | 0 | 0 |

Lipase inhibition is shown in %

Figure 3:
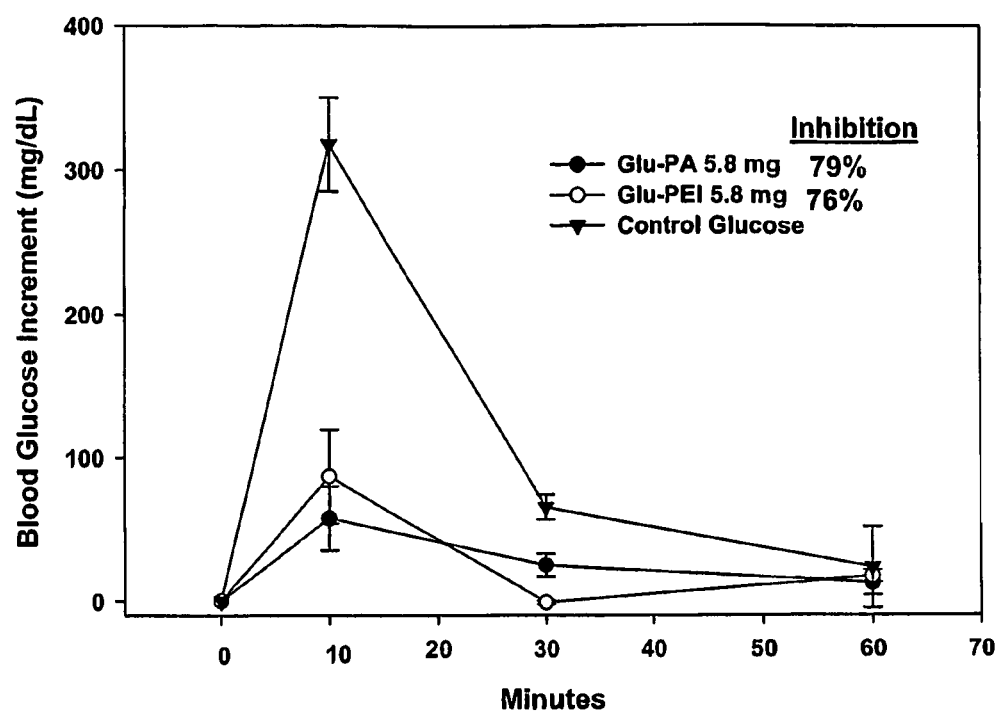
FIG. 3 is a graph showing the effect of PA-Glu and PEI-Glu on glucose absorption in C57B 1/6 mice.

Inhibition of glucose transport in C57B1/6 mice was measured as described in Example 8.2 and the results are shown in FIG. 3.

EQUIVALENTS

While this invention has been particularly revealed and described with references to preferred embodiments thereof, it will be explicit to those skilled in the art that various changes in form and details may be made therein without departing from the spirit and scope of the invention as defined by the appended claims. Those skilled in the art will know or be able to establish using no more than routine experimentation, many equivalents to the specific embodiments of the invention described specifically herein. Such equivalents are intended to be encompassed in the scope of the claims.

The invention claimed is:

1. A method of treating a condition which benefits from reduced glucose absorption in the intestine or reduced dietary triglyceride metabolism, comprising administering to a subject with the condition an effective amount of alginate having a glucopyranosyl or galactopyranosyl moiety covalently linked thereto, wherein said glucopyranosyl or galactopyranosyl moiety can occupy the gluco-binding pocket of sodium-dependent glucose transporter.

2. The method according to claim 1, wherein said condition is selected from the group consisting of obesity, hyperlipaemia, type II diabetes, type I diabetes, hyperglycemia, hyperinsulinemia, hypertriglyceridemia, Metabolic Syndrome, dumping syndrome and atherosclerosis.

3. A method of preventing weight gain or aiding weight loss in a subject which comprises administration to said subject of a compound according to claim 1.

* * * * *